United States Patent [19]

Gibson et al.

[11] Patent Number: 5,028,721

[45] Date of Patent: Jul. 2, 1991

[54] BIS(FUNCTIONALLY-SUBSTITUTED PHENYLENE) SEMI-RIGID CROWNS AND PROCESS FOR MAKING

[75] Inventors: Harry W. Gibson; Yadollah Delaviz, both of Blacksburg, Va.

[73] Assignee: Virginia Tech Intellectual Properties, Inc., Blacksburg, Va.

[21] Appl. No.: 418,362

[22] Filed: Oct. 6, 1989

[51] Int. Cl.[5] .......................................... C07D 323/00
[52] U.S. Cl. .................................................. 549/352
[58] Field of Search ........................................ 549/352

[56] References Cited

FOREIGN PATENT DOCUMENTS 2207267 9/1987 Japan .

*Primary Examiner*—C. Warren Ivy
*Assistant Examiner*—Amelia A. Owens
*Attorney, Agent, or Firm*—Richard P. Fennelly; Louis A. Morris

[57] ABSTRACT

Bis(carboalkoxy-substituted phenylene)-32-crown-10 compounds, useful as polymerizable monomers, can be formed by first reacting a functionalized dihydroxy aromatic compound with a hydroxy protecting group-substituted halopolyether, deprotecting the resulting product to form the diol, forming the corresponding tosylate, and reacting the tosylate with the same or analogous diol in a cyclization reaction to form the crown ether compound.

6 Claims, No Drawings

BIS(FUNCTIONALLY-SUBSTITUTED PHENYLENE) SEMI-RIGID CROWNS AND PROCESS FOR MAKING

BACKGROUND OF THE INVENTION

It has recently been suggested that a family of polymeric analogs to macromolecules, termed "polyrotoxanes", be synthesized using crown ethers (or macrocyclic polyethers) as the cyclic component thereof. See H. W. Gibson et al., Polymer Preprints, 1988, 29(1) 248-249 and P. R. Lecavalier et al., Polymer Preprints, 1989, 30(1) 189-190.

It is known to form hetero crown ethers (also termed "corands") comprising oxygen atoms separated by $(CH_2)_n$ groups and groups of the ortho-phenylene type. See C. J. Pedersen, J. Am. Chem. Soc. 89 (1967) 2495 and 7017.

Chapoteau et al., in J. Org. Chem. 1989, 54, 861-867 mention that crown ethers (corands) based on the 1,3-xylyl subunit have been synthesized with a variety of intraannular or inward facing groups including methoxyl, phenolic, carboxyl, methoxycarbonyl, hydroxyl, nitrile and sulfins.

Moore et al. in J. Amer. Chem. Soc. 99:19, 6398-6410 (1977) show certain monobenzo-crown ethers containing outwardly facing substituents such as —$CH_2C_2H_5$ and —CN.

Allwood et al., in a series of reports in J. Chem. Soc., Chem. Commun., 1987, 1054-1064 illustrate a dinaphthyl-crown ether (DN30C10 on pp. 1054-1058), a non-substituted bismetaphenylene-32-crown-10 derivative (BMP32C10) on pp. 1058-1061, and a bisparaphenylene-34-crown-10 derivative (BPP34C10) on pp. 1061-1064. The BMP32C10 derivative was synthesized by partial benzylation of resorcinol to yield 3-benzyloxyphenol which was reacted with tetraethylene glycol bis(toluene-p-sulfonate) (TEGBT) to yield 1,11-bis(3'-benzyloxyphenoxy)-36,9-trioxaundecane. Deprotection of that product followed by reaction of the derived diphenol with TEGBT afforded the BMP32C10 derivative.

DESCRIPTION OF THE INVENTION

The present invention relates to a novel class of "functionalized" dibenzo-crown ether compounds, e.g., those which may be broadly considered to be bis(carboalkoxysubstituted phenylene) crown ethers, specifically, bis(carboalkoxy-substituted phenylene) 32-crown-10 compounds. The term "functionalized" as used herein is intended to cover substituents on the dibenzo moieties that are outwardly facing or "interannular" so as to be capable of reaction with other monomeric compounds to form polymers, such as polyesters, polyamides, polyimides and the like. Examples of such substituents include—COOH,—COCl,—OH,—R-OH (where R is alkylene or arylene),—$NH_2$, or—R—$NH_2$ (where R is alkylene or arylene).

The process used herein is one in which a functionalized dihydroxy aromatic compound is reacted with a halopolyether (e.g., a chloropolyether) containing a hydroxy protecting group at one end thereof, such as tetrahydropyranyl to form an initial reaction product.

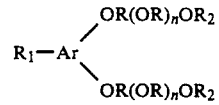

where $R_1$ —$OR(OR)_nOR_2$ denotes the functional group, Ar denotes the phenylene ring, and is derived from the halopolyether with R being alkylene (e.g., ethylene), n being from 1 to 8, and $R_2$ being the protective group. The reaction conditions can be as follows: sodium hydride (NaH) as base, dimethylformamide as solvent at 25° to 100° C. for up to five days under an inert gas (e.g., nitrogen).

The reaction product is then acid-catalysis deprotected under inert gas (e.g., nitrogen) to form the corresponding diol upon removal of the protective group $R_2$.

The resulting diol is then reacted with tosyl halide (e.g., tosyl chloride) using an amine acid acceptor in order to form the corresponding tosylate.

The cyclization reaction to form the final crown ether product is accomplished by reacting the foregoing tosylate with the previously described diol, e.g., (or an analogous diol with n being of a different value) in the presence of an alkali metal hydride in an appropriate solvent (e.g., tetrahydrofuran). The final product can be envisioned as having the formula:

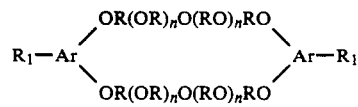

where $R_1$, Ar, R, and n are as described above. In the case of a 32-crown-10 product, n will be equal to 1.

The instant invention is illustrated by the Examples which follow.

EXAMPLE 1

This Example illustrates formation of methyl 3,5-bis(5-tetrahydropyranyloxy-3-oxa-1-pentyloxy)benzoate.

A solution of 40.4 gm (0.193 mole) of 2-(2'-chloroethoxy)-ethyltetrahydropyranyl ether in 85 ml of dry dimethylformamide was added dropwise to a mixture of 10 gm (0.06 mole) of methyl 3,5-dihydroxybenzoate and 3.0 gm (0.125 mole) of sodium hydride in 180 ml dimethylformamide at 80° C. under a blanket of dry nitrogen. The resulting mixture was stirred at 80° C. for fifteen hours and an additional 1.04 gm (0.043 mole) of sodium hydride was added. After an additional fifteen hours at 80° C. the cold reaction mixture was filtered from sodium chloride and solvent was removed by vacuum to yield a brown viscous oil residue which was extracted with ethyl ether (100 ml) three times. The organic layer was dried over magnesium sulfate, filtered, and solvent was removed to produce a viscous oil (90% yield).

IR (neat): 1723 (C=O); and 1130 cm$^{-1}$ (O-C-O).

$^1$H NMR (CDCl$_3$/(tetramethylsilane) TMS): delta 1.3-1.9 (12H, m, R-H), 3.35-4.3 (13H, m,—$CH_2O$—, and $CH_3OCO$), 4.6 (2H, s,—OCHO—), and 6.6-7.2 (3H, m, Ph-H).

EXAMPLE 2

A solution of 60 0 gm (0.117 mole) of the bis(tetrahydropyranyl) ether from Example 1 was deprotected to form the diol by being placed in 600 ml of $CH_2$: methanol (1:1 v/v) and combined with 6 ml concentrated hydrochloric acid. The mixture was stirred at room temperature for five hours. The solution mixture was neutralized with saturated sodium bicarbonate, the organic phase was dried over magnesium sulfate, was filtered and solvent was removed under vacuum. A viscous oil was produced in 95% yield.

IR (neat): 3405 (O-H), 1723 (C=O), and 1130 cm$^{-1}$ (O-C-O).

$^1$H NMR (CDCl$_3$): delta 2.95 (2H, br, S, OH), 3.6–4.4 (19H,—CH$_2$O—and CH$_3$OCO), and 6.6–7.3 (3H, in, Ph-H).

EXAMPLE 3

This Example illustrates formation of methyl 3,5-bis(5-toluenesulfonyloxy-3-oxa-1-pentyloxy)-benzoate.

Separate solutions of 15.0 gm (0.043 mole) of diol from Example 2 in 9 ml dry pryidine and 25.0 gm (0.13 mole) of para-toluenesulfonyl chloride in 115 ml of pyridine were cooled to $-2°$ C. The solutions were then combined and maintained at $-20°$ C. for seventy-six hours. The reaction mixture wa extracted with three 175 ml volumes of dichloromethane. The combined organic phases were washed with three 250 ml volumes of ice cold 6N aqueous hydrochloric acid and 175 ml of saturated aqueous ammonium chloride. After drying the organic phase over magnesium sulfate and filtration, the solvent was removed under reduced pressure yielding a viscous yellow oil (96.5% yield).

IR (neat): 1355, 1190, and 1175 (S=O), and 1723 cm$^{-1}$ (C=O).

$^1$H NMR (CDCl$_3$/TMS): delta 2.4 (6H, s, Ph-CH$_3$); 3.6–4.3 (19H, m,—CH$_2$O—, CH$_3$OCO), 6.6–7.3 (3H, m, Ph-H), and 7.55 (8H, ABq,—SO$_2$—Ph—H).

EXAMPLE 4

This Example illustrates formation of bis(5-carbomethoxy1,3-phenylene)-32-crown-10.

To a solution of the diol of Example 2 (4.74 gm, 0.013 mole) in dry tetrahydrofuran (225 ml) was added 1.32 gm (0.055 mole) of sodium hydride and the solution was stirred under dry nitrogen for one hour. A solution of the ditosylate from Example 3 (8.9 gm, 0.013 mole) in 111 ml of tetrahydrofuran was added, and the mixture was stirred at room temperature for five days and was then refluxed for thirty-six hours. The solution was cooled to room temperature, filtered, and the solvent was evaporated in vacuo. The resulting residue was partitioned between $CH_2Cl_2$ (100 ml) and water (100 ml). The organic layer was dried over magnesium sulfate and was evaporated. The residue (6.5 gm) was purified by column chromatography on acidic alumina with ethyl acetate-petroleum ether (2:1) as eluent to produce 2.2 gm (24% of ester).

IR (KBr pellet): 1723 (C=O), and 1130 cm$-1$ (O-C-O)

$^1$H NMR (CDCl$_3$/TMS): delta 3.6–4.3 (38H, m, OCH$_2$ and CH$_3$OCO), and 6.6–7.3 (3H, m, Ph-H).

We claim:

1. A process for the formation of a functionalized dibenzo-crown ether capable of polymer formation which comprises:
    (a) reaction of a functionalized dihydroxy aromatic compound with a hydroxy protecting group-substituted halopolyether;
    (b) acid-catalyzed deprotection of the product from (a) to form the corresponding diol upon removal of the hydroxy protecting group therefrom;
    (c) reaction of the product from step (b) with tosyl halide to form the corresponding tosylate; and
    (d) cyclization of the product from step (c) by reaction with the product of step (b) to form a functionalized dibenzo-crown ether.

2. A process as claimed in claim 1 wherein the hydroxy protecting group-substituted halopolyether is of the formula XR'OR'OTHP where X is halo, R' is alkylene, and THP is tetrahydropyranyl as the hydroxy protecting group.

3. A process as claimed in claim 2 wherein X is chloro and R' is ethylene.

4. A process as claimed in claim 1 wherein the functionalized dibenzo-crown ether is a carboalkoxy-substituted 1,3-phenylene-32 crown-10 ether.

5. A process as claimed in claim 3 wherein the functionalized dibenzo-crown ether is a carboalkoxy-substituted 1,3-phenylene-32-crown-10 ether.

6. A process as claimed in claim 1 wherein the functionalized dibenzo-crown ether is a bis(5-carboalkoxy-1,3-phenylene)- 32-crown-10.

* * * * *